(12) United States Patent
Doshi

(10) Patent No.: US 7,915,593 B2
(45) Date of Patent: Mar. 29, 2011

(54) IMAGE CHANNEL CODING

(75) Inventor: Niraj K. Doshi, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 907 days.

(21) Appl. No.: 11/833,647

(22) Filed: Aug. 3, 2007

(65) Prior Publication Data
US 2009/0033776 A1 Feb. 5, 2009

(51) Int. Cl.
*H04N 9/09* (2006.01)
(52) U.S. Cl. .............................. 250/370.06; 250/370.09
(58) Field of Classification Search ............ 250/370.06, 250/370.09, 369
See application file for complete search history.

(56) References Cited

U.S. PATENT DOCUMENTS

| | | | | |
|---|---|---|---|---|
| 3,594,577 | A | * | 7/1971 | Loveday ....................... 250/366 |
| 5,293,044 | A | * | 3/1994 | Klingenbeck-Regn et al. ............................ 250/369 |
| 6,362,478 | B1 | * | 3/2002 | McDaniel et al. ......... 250/361 R |

* cited by examiner

*Primary Examiner* — Tony Ko
(74) *Attorney, Agent, or Firm* — Peter L. Kendall

(57) ABSTRACT

A photo detector matrix may have a plurality of photo detectors arranged in a matrix each generating an output signal, and a plurality of wires coupled with the photo detectors, wherein a number of wires is less than a number of photo detectors and the plurality of photo detectors are assigned to the plurality of wires such that signals generated by the plurality of photo detectors encode a location of a light peak applied to the photo detector matrix.

26 Claims, 2 Drawing Sheets

# IMAGE CHANNEL CODING

TECHNICAL FIELD

The present invention is related to coding, more specifically the present invention is related to image signal coding.

BACKGROUND

Many electronic devices may generate a plurality of signals that need to be transmitted internally or externally. To avoid a high number of signal lines a variety of coding and multiplexing schemes are known in the art. Their applicability depends on the specific technology and, thus, allow more or less reduction in necessary signal wires.

In particular in the field of medical image technology such as Positron Emission Tomography (PET) or gamma cameras, at least one photo detector matrix is used. In a PET scanner, a high number of photomultiplier tubes (PMT) is usually arranged in a circle. To conduct a so-called PET scan, a short-lived radioactive tracer isotope, which decays by emitting a positron, is injected usually into the blood circulation of a living subject. After the metabolically active molecule becomes concentrated in tissues of interest, the research subject or patient is placed in the imaging scanner. The molecule most commonly used for this purpose is fluorodeoxyglucose (FDG), a sugar, for which the waiting period is typically an hour.

As the radioisotope undergoes positron emission decay, it emits a positron, the antimatter counterpart of an electron. After traveling up to a few millimeters the positron encounters and annihilates with an electron, producing a pair of gamma photons moving in almost opposite directions. These are detected when they reach a scintillator material in the scanning device, creating a burst of light which is detected by photomultiplier tubes (PMT) or silicon avalanche photodiodes (Si APD). The technique depends on simultaneous or coincident detection of the pair of photons.

The raw data collected by a PET scanner are a list of 'coincidence events' representing near-simultaneous detection of annihilation photons by a pair of detectors. Each coincidence event represents a line in space connecting the two detectors along which the positron emission occurred. Coincidence events can be grouped into projections images, called sinograms. The sinograms are sorted by the angle of each view and tilt, the latter in 3D case images. The sinogram images are analogous to the projections captured by computed tomography (CT) scanners, and can be reconstructed in a similar way.

A PMT can be used in many imaging systems, such as PET scanners and gamma cameras. Each PMT produces one or more signals that need to be processed to generate an image from a plurality of single events that are detected by a PMT. The processing of these signals is performed either internally or these signals are transmitted to an external processing station. In modern PET scanners each PMT may generate a plurality of signals, e.g., a PMT may be able to differentiate as many as 256 different positions and thus would require as many signal wires to identify each specific geometric position within the matrix of scintillator crystals. Thus, a high number of wires is required to transmit these signals.

Thus, there exists a need for an improved multiplexing scheme for transmitting analog digital signals associated with a specific location.

SUMMARY

According to an embodiment, a photo detector matrix may comprise a plurality of photo detectors arranged in a matrix each generating an output signal, a plurality of wires coupled with the photo detectors, wherein a number of wires is less than a number of photo detectors and the plurality of photo detectors are assigned to the plurality of wires such that signals generated by the plurality of photo detectors encode a location of a light peak applied to the photo detector matrix.

According to another embodiment, an imaging system may comprise at least one photo detector matrix comprising a plurality of photo detectors arranged in a matrix each generating an output signal, and a plurality of wires coupled with the photo detectors, wherein a number of wires is less than a number of photo detectors and the plurality of photo detectors are assigned to the plurality of wires such that signals generated by the plurality of photo detectors encode a location of a light peak applied to the photo detector matrix.

According to yet another embodiment, a method for encoding a location in signals generated by a plurality of photo detectors arranged in a matrix, may comprise the steps of providing n wires, wherein n is smaller than the number of photo detectors; and coupling each photo detector with one of the n wires, wherein each photo detector of the matrix and its surrounding photo detectors are assigned to a unique permutation of the n wires.

BRIEF DESCRIPTION OF THE DRAWINGS

A more complete understanding of the present disclosure thereof may be acquired by referring to the following description taken in conjunction with the accompanying drawings wherein.

Figure 1:
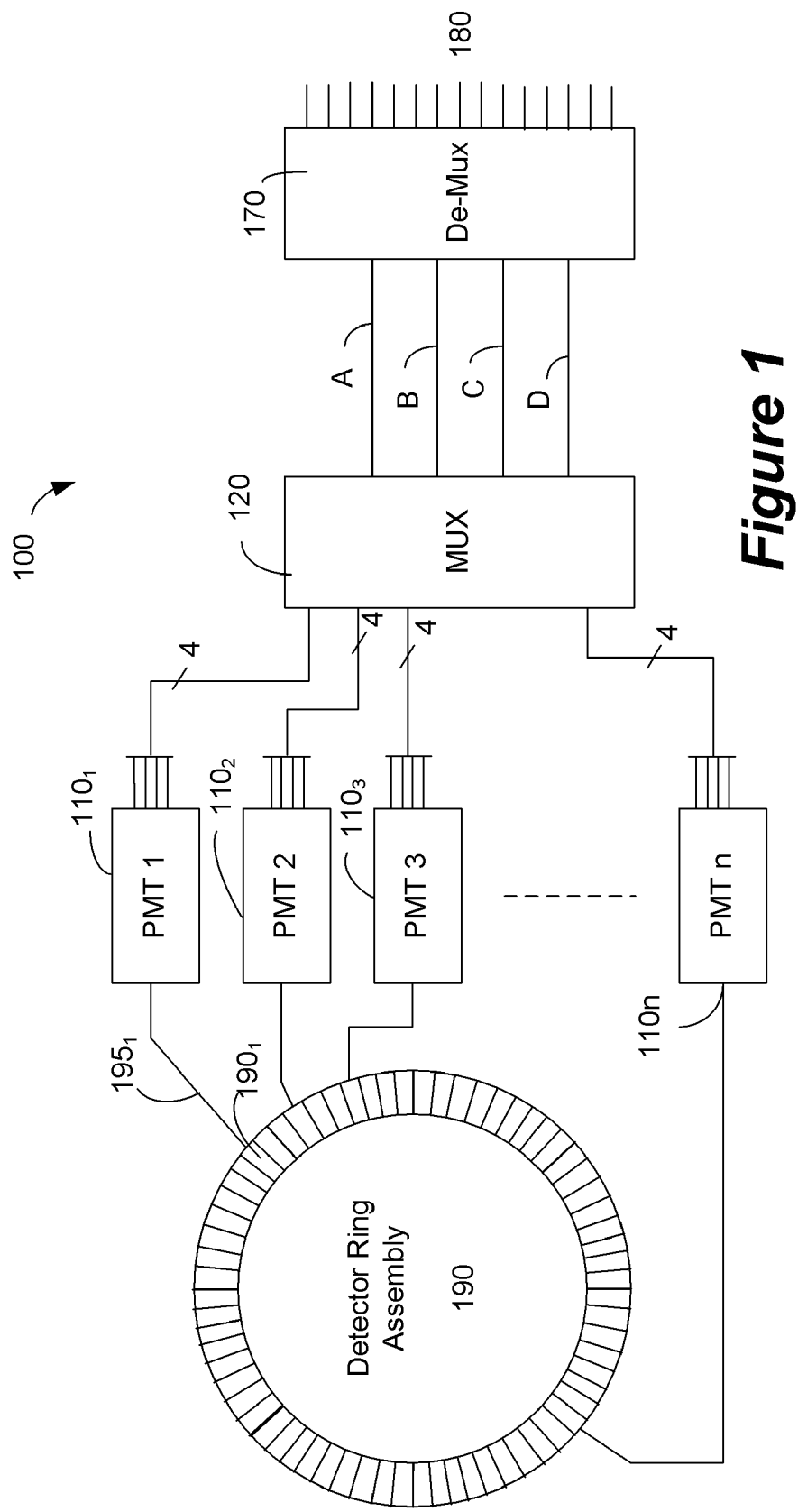
FIG. 1 shows a simplified block diagram of an embodiment of parts of a PET scanner.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

As stated above, according to an embodiment, a photo detector matrix may comprise a plurality of photo detectors arranged in a matrix each generating an output signal, and a plurality of wires coupled with the photo detectors, wherein a number of wires is less than a number of photo detectors and the plurality of photo detectors are assigned to the plurality of wires such that signals generated by the plurality of photo detectors encode a location of a light peak applied to the photo detector matrix.

An imaging system may comprise at least one or a plurality of such a photo matrix. According to an embodiment, the photo detector matrix may comprise n wires allowing for m permutations and wherein each matrix location is assigned to a permutation defined by a plurality of surrounding matrix locations. According to an embodiment, a permutation may comprise a matrix photo detector and its horizontally and vertically adjacent photo detectors or a matrix photo detector and its horizontally, vertically, and diagonally adjacent photo detectors. According to yet another embodiment, a permutation may comprise a corner matrix photo detector and one horizontally and one vertically adjacent photo detector and another permutation may comprise a center matrix photo detector and two horizontally and two vertically adjacent photo detector. According to yet another embodiment, a permutation may also comprise a corner matrix photo detector and one horizontally, one vertically, and one diagonally adjacent photo detector and another permutation may comprise a center matrix photo detector and two horizontally, two vertically, and four diagonally adjacent photo detector. According to a further embodiment, an imaging system may also comprise a multiplexer having a plurality of inputs, each input coupled with the plurality of wires of each photo detector matrix.

FIG. 1 shows an embodiment of relevant parts of a PET scanner 100. A detector ring assembly 190 comprises a plurality of scintillator matrices $190_n$ that are each coupled with a photomultiplier tube $110_n$ through respective optically couplings $195_n$. According to one embodiment, each photomultiplier $110_n$ is arranged directly behind an associated scintillator matrix $190_n$. Each scintillator matrix $190_n$ may have a plurality of scintillators arranged in a matrix. The matrix, thus, can receive a geographic maximum light peak within said matrix that needs to be detected. Each PMT $110_n$ may have a plurality of photo detectors, for example each scintillator crystal may have an associated photo detector matrix. This photodetector matrix may coincide with the scintillator matrix bus does not need to. In some embodiments, less or more photo detectors than scintillators are used and a detector unit may determine from the photo detector matrix signals which associated scintillator crystal produced the highest output signal. The photomultipliers $190_n$ of the detector ring assembly 190, thus, can generate a plurality of signals in parallel that need to be transmitted for further processing.

According to an embodiment, in an arrangement in which a photo detector provides for a unique geographic signal each PMT comprises a set of output wires carrying the signals from each PMT using a unique transmission scheme which encodes the geographic location into the signal. In the embodiment shown in FIG. 1, four wires are used to encode the geographic location and the output signals of the photo detectors as will be explained in detail below. Other embodiments may use more or less wires per PMT.

Each set of output signals can then be transmitted further through a multiplexer 120, transmission path A, B, C, D and de-multiplexer 170. Thus, a remote data processing station (not shown) will be able to decode the transmission scheme and determine the specific location from which the respective signal was generated.

Thus, a transmission path requires only a minimum of for example k wires to be able to encode a signal amplitude and a location. As stated above, FIG. 1 shows an example for k=4, in which wires A, B, C, D are used and coupled through multiplexer 120 with the respective PMT's $110_n$ of the PET scanner 100. A remote de-multiplexer 170 receives these signals and a respective processing unit can then decode the location and generate the associate output signal for that location from the transmitted signal information.

Figure 2:
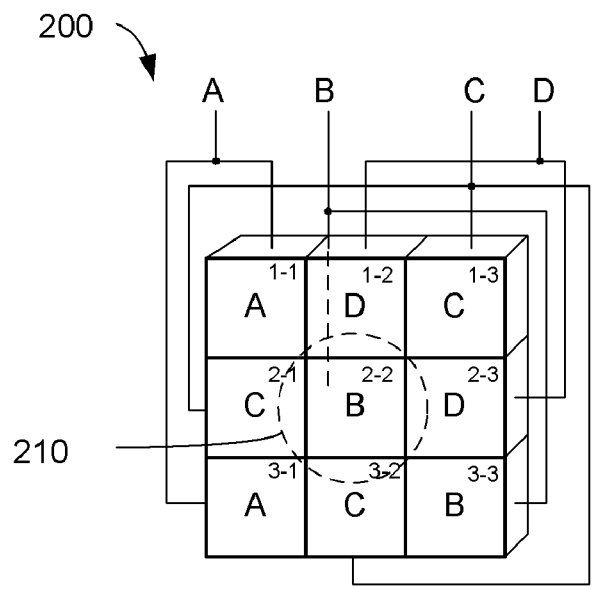
FIG. 2 illustrates an embodiment of an encoding scheme.

According to an embodiment, permutations are used to provide for an encoding scheme of signals that allows for a unique identification of associated location. FIG. 2 shows an example of a 3 by 3 photo detector matrix which can, for example, provide for 9 distinct locations 1-1, 1-2, ... 3-3. In case a light pulse generated by an associated scintillator matrix produces a peak in the upper left corner, i.e. photo detector 1-1, then the surrounding photo detectors will also receive a certain amount of light depending on the area covered by the light pulse. FIG. 2 shows a possible area 210 covered by a light pulse generated in the center cell 2-2. However, such areas may be larger. The coding scheme used according to an embodiment, takes advantage of this fact and assigns multiple photo detectors to single transmission wires according to a unique scheme. For example, as shown in FIG. 2 photo detectors 1-1 and 3-1 are assigned to wire A and their output signals will, thus, be summed up in transmission wire A. Similarly, photo detectors 2-2 and 3-3 are assigned to wire B, photo detectors 1-3, 2-1, and 3-2 to wire C, and photo detectors 1-2 and 2-3 to wire D. Other assignments schemes can be selected as will be explained below.

By choosing a unique assignment, each light pulse having a coverage area 210 will produce a different unique output signal on the four wires A, B, C, and D. Assuming, that only photo detectors in direct proximity to a peak location generate an output signal shows that location 1-1 would generate a strong signal in photo detector 1-1 and a lesser strong signal in photo detectors 1-2, and 2-1. Photo detector 2-2 would carry an ever lesser or no signal. However, if a larger area is covered by a light pulse then photo detectors 1-1, 1-2, 2-1, and 2-2 would generate respective larger signals. Assuming a coverage area 210 for each associated scintillator, as shown in FIG. 1, the following list shows output signal for each wire under such an assumption.

| Location | Signals |
| --- | --- |
| 1-1 | A B C D |
| 1-2 | A B 2C 2D |
| 1-3 | B C 2D |
| 2-1 | 2A B 2C D |
| 2-2 | 2A 2B 3C 2D |
| 2-3 | 2B 2C 2D |
| 3-1 | A B 2C |
| 3-2 | A 2B 2C D |
| 3-3 | 2B C D |

As can be seen, in each scenario, each peak location generates a unique pattern of signals in wires A, B, C, and D. Some locations have assigned multiple photo cells to one wire. For example, a peak in location 1-3 will produce additional signals in photo detectors 1-2 and 2-3 which are both assigned to wire D. Thus, the sum of the output signals of photo detectors 1-2 and 2-3 will be carried on wire D. This is indicated by "2D" in the list. Even though, some locations might generate signals on all four wires, the weighting of the signals will be unique as a peak in location 1-3 will have stronger signals on wire C than on wires B and D and no signal on wire A.

According to an embodiment, a scintillator matrix may have a corresponding photo detector matrix. However, the photo detector matrix does not need to have the same number of cells as the scintillator matrix. The photo detector matrix can, for example, have more cells and, thus, a finer resolution. Accordingly, the coverage area of a light pulse can be larger.

The photo detectors surrounding a peak location will receive usually less light. Thus, assuming for example a 75% drop in light intensity for adjacent cells when assuming a light coverage 210, the following Table 1 shows the signal weighting for each peak location. For cells which are adjacent in a diagonal direction, such as cells 1-1 and 2-2, a 90% drop is assumed Table 1 is normalized in such a way that a peak light pulse is assumed as 1 and a horizontally or vertically surrounding photo detector would generate a value of 0.25 and a diagonally surrounding photo detector would generate a value of 0.1 in this assumption. However, other percentages may apply.

TABLE 1

| Location | A | B | C | D |
|---|---|---|---|---|
| 1-1 | 1 | 0.1 | 0.25 | 0.25 |
| 1-2 | 0.25 | 0.25 | 0.35 | 1.1 |
| 1-3 | 0 | 0.1 | 1 | 0.5 |
| 2-1 | 0.5 | 0.25 | 1.1 | 0.1 |
| 2-2 | 0.2 | 1.1 | 0.6 | 0.5 |
| 2-3 | 0 | 0.5 | 0.35 | 1.1 |
| 3-1 | 1 | 0.1 | 0.5 | 0 |
| 3-2 | 0.25 | 0.5 | 1.1 | 0.1 |
| 3-3 | 0 | 1.1 | 0.25 | 0.25 |

As can be seen unique patterns are created through the specific assignment of the wires to the respective photo detectors. Thus, depending on the association of scintillators and photo detectors and the coverage area of a light pulse, other assignments will generate other unique patterns which can be analyzed by a processor. Hence, if unique patterns are assigned, from a respective signal pattern a processor can reconstruct the location in the matrix of a PMT. Moreover, if less permutations are used than available by the number of wires, a certain redundancy can be achieved which improves the decoding and reliability of each location detection.

Taking only the immediate adjacent cells surrounding a peak location into consideration, the number of wires will define how many locations can be encoded. Again, if no weighting of the signals is considered as discussed in the first example above, the different permutations that can be created depend on the location. For example, the corner locations 1-1, 1-3, 3-1, and 3-3 each have two or three surrounding photo detectors depending on the light pulse coverage area. Thus, permutations having four elements selectable out of the group of wires A, B, C, and D apply. The side locations 1-2, 2-1, 2-3, and 3-2 have 3 or 5 surrounding photo detectors depending on the light pulse coverage area. Thus, permutations having four or six elements selectable out of the group of wires A, B, C, and D apply. Finally, the center location is surrounded by four or 8 photo detectors depending on the light pulse coverage area. Thus, permutations having 5 or 9 elements selectable out of the group of wires A, B, C, and D apply.

The number of wires necessary depends on the many factors. For example, the size of the photo detector matrix, the number of affected cells per light pulse, and the redundancy requirements for ensuring that each location can be uniquely identified.

Figure 3:
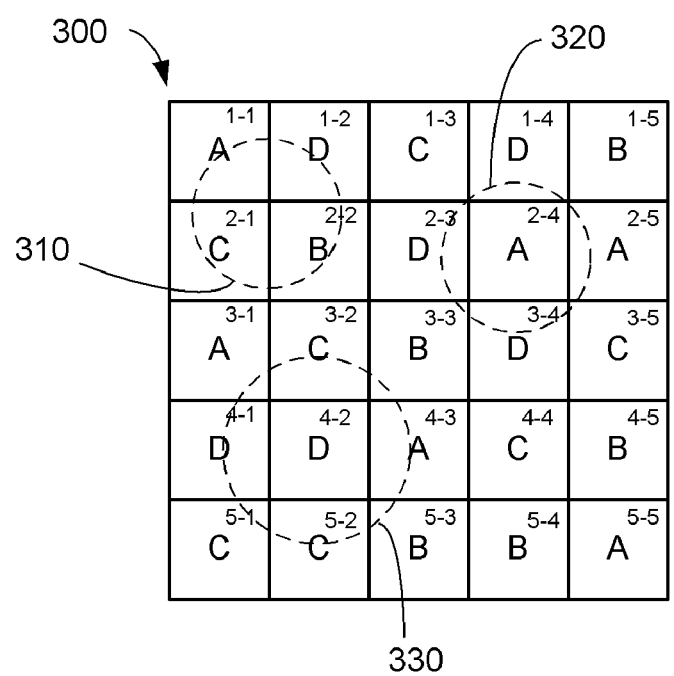
FIG. 3 illustrates another embodiment of an encoding scheme.

FIG. 3 shows a possible arrangement with a 5×5 matrix of photo detectors. Again, four wires are used to encode the location into the output signal of the photo detectors. In this embodiment the same type of peak locations exist as in the example of the 3×3 matrix. The corner locations all have 3 surrounding photo diodes similar as in FIG. 2. However, there exist more side location with five surrounding photo detectors and more center locations with eight surrounding photo detectors. Thus, even more permutations would be possible. Thus, four wires will allow for a plurality of encoding permutations that still provides for sufficient redundancy.

The following assumes again a scintillator matrix corresponding to the light detector matrix and a light coverage area as shown with circle 320. In case of this 5×5 matrix, a peak generated in the bottom right corner 5-5 would obtain only signals in signal wires A and B. There would be no signal or a very small signal in wire C and no signal in wire D. However, if there would be signals coming from wires A, B, and D, then the location of the peak would be in the upper right corner 1-5 and signals on all wires would indicate a peak in the upper left corner. Moreover, due to decreasing signal strength outside the actual peak area, a weighting of the signals as explained above in connection with the 3×3 matrix would provide for even more attributable uniqueness of a pattern. Again, the following Table 2 shows such a pattern weighting assuming the horizontally and vertically surrounding photo detectors receive a 25% light intensity and the diagonally surrounding photo detectors a 10% light intensity. However, as discussed above, other distribution percentages might apply.

TABLE 2

| Location | A | B | C | D |
|---|---|---|---|---|
| 1-1 | 1 | 0.1 | 0.25 | 0.25 |
| 1-2 | 0.25 | 0.25 | 0.35 | 1.1 |
| 1-3 | 0.1 | 0.1 | 1 | 0.75 |
| 1-4 | 0.35 | 0.25 | 0.25 | 1.1 |
| 1-5 | 0.35 | 1 | 0 | 0.25 |
| 2-1 | 0.5 | 0.25 | 1.1 | 0.1 |
| 2-2 | 0.2 | 1.1 | 0.6 | 0.5 |
| 2-3 | 0.25 | 0.5 | 0.35 | 1.3 |
| 2-4 | 1.25 | 0.2 | 0.2 | 0.75 |
| 2-5 | 1.25 | 0.25 | 0.1 | 0.2 |
| 3-1 | 1 | 0.1 | 0.5 | 0.35 |
| 3-2 | 0.35 | 0.5 | 1.1 | 0.2 |
| 3-3 | 0.35 | 1.1 | 0.35 | 0.6 |
| 3-4 | 0.45 | 0.35 | 0.5 | 1.1 |
| 3-5 | 0.35 | 0.25 | 1.1 | 0.25 |
| 4-1 | 0.25 | 0 | 0.45 | 1.1 |
| 4-2 | 0.35 | 0.2 | 0.5 | 1.1 |
| 4-3 | 1 | 0.6 | 0.45 | 0.35 |
| 4-4 | 0.35 | 0.7 | 1.1 | 0.25 |
| 4-5 | 0.25 | 1.1 | 0.5 | 0.1 |
| 5-1 | 0 | 0 | 1.25 | 0.35 |
| 5-2 | 0.1 | 0.25 | 1.1 | 0.35 |
| 5-3 | 0.25 | 1.1 | 0.35 | 0.1 |
| 5-4 | 0.35 | 1.35 | 0.25 | 0 |
| 5-5 | 1 | 0.5 | 0.1 | 0 |

Again, each location will generate a unique pattern which can be analyzed by a respective processor. As stated above, the scintillator matrix does not need to coincide with the photo detector matrix. FIG. 3 shows another light pulse coverage area 310 whose center does not correspond with the center of a cell and coverage area 330 which is larger. Such light pulses 310 and 330 could be generated by other arrangements and are merely shown to demonstrate which photo detectors would be affected by a different placements or sizes.

This technique of encoding the location can be used with PET scanners as well as gamma cameras and any other equipment that comprises a matrix of photo cells for which the location and signal strength need to be processed. For example, one can potentially use this technique for a multitude of imaging applications that require a number of signals to be digitized and associated with a unique location.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A photo detector matrix comprising:
    a plurality of photo detectors arranged in a matrix each generating an output signal,
    a plurality of wires coupled with the photo detectors in a predetermined arrangement to differentiate signals occurring in an event photo detector from those signals in photo detectors contiguous to the event photo detector, wherein a number of wires is less than a number of photo detectors and the plurality of photo detectors are assigned to the plurality of wires such that signals generated by the plurality of photo detectors encode a location of a light peak applied to the photo detector matrix, wherein the encoded location comprises a signal pattern that differentiates an event photo detector from photo detectors contiguous to the event photo detector.

2. The photo detector matrix according to claim 1, comprising n wires allowing for m permutations and wherein each matrix location is assigned to a permutation defined by a plurality of surrounding matrix locations.

3. The photo detector matrix according to claim 2, wherein a permutation comprises a matrix photo detector and its horizontally and vertically adjacent photo detectors.

4. The photo detector matrix according to claim 2, wherein a permutation comprises a matrix photo detector and its horizontally, vertically, and diagonally adjacent photo detectors.

5. The photo detector matrix according to claim 3, wherein a permutation comprises a corner matrix photo detector and one horizontally and one vertically adjacent photo detector.

6. The photo detector matrix according to claim 3, wherein a permutation comprises a center matrix photo detector and two horizontally and two vertically adjacent photo detectors.

7. The photo detector matrix according to claim 4, wherein a permutation comprises a corner matrix photo detector and one horizontally, one vertically, and one diagonally adjacent photo detector.

8. The photo detector matrix according to claim 4, wherein a permutation comprises a center matrix photo detector and two horizontally, two vertically, and four diagonally adjacent photo detector.

9. An imaging system comprising:
    at least one photo detector matrix comprising:
        a plurality of photo detectors arranged in a matrix each generating an output signal, and
        a plurality of wires coupled with the photo detectors in a predetermined arrangement to differentiate signals occurring in an event photo detector from those signals in photo detectors contiguous to the event photo detector, wherein a number of wires is less than a number of photo detectors and the plurality of photo detectors are assigned to the plurality of wires such that signals generated by the plurality of photo detectors encode a location of a light peak applied to the photo detector matrix, wherein the encoded location comprises a signal pattern that differentiates an event photo detector from photo detectors contiguous to the event photo detector.

10. The imaging system according to claim 9, wherein the photo detector matrix comprises n wires allowing for m permutations and wherein each matrix location is assigned to a permutation defined by a plurality of surrounding matrix locations.

11. The imaging system according to claim 10, wherein a permutation comprises a matrix photo detector and its horizontally and vertically adjacent photo detectors.

12. The imaging system according to claim 10, wherein a permutation comprises a matrix photo detector and its horizontally, vertically, and diagonally adjacent photo detectors.

13. The imaging system according to claim 11, wherein a permutation comprises a corner matrix photo detector and one horizontally and one vertically adjacent photo detector.

14. The imaging system according to claim 11, wherein a permutation comprises a center matrix photo detector and two horizontally and two vertically adjacent photo detector.

15. The imaging system according to claim 12, wherein a permutation comprises a corner matrix photo detector and one horizontally, one vertically, and one diagonally adjacent photo detector.

16. The imaging system according to claim 12, wherein a permutation comprises a center matrix photo detector and two horizontally, two vertically, and four diagonally adjacent photo detector.

17. The imaging system according to claim 9, further comprising a multiplexer having a plurality of inputs, each input coupled with the plurality of wires of each photo detector matrix.

18. The imaging system according to claim 9, wherein the imaging system is positron emission tomography (PET) scanner comprising:
    ring detector assembly;
    a plurality of scintillator matrices, and
    a plurality of photo detector matrices.

19. The imaging system according to claim 9, wherein the imaging system is a gamma camera.

20. A method for encoding a location in signals generated by a plurality of photo detectors arranged in a matrix, the method comprising the steps of:
    providing n wires, wherein n is smaller than the number of photo detectors;
    coupling each photo detector with one of the n wires in a predetermined arrangement to differentiate signals occurring in an event photo detector from those signals in photo detectors contiguous to the event photo detector, wherein each photo detector of the matrix and its surrounding photo detectors are assigned to a unique permutation of the n wires to provide an encoded location, wherein the encoded location comprises a signal pattern that differentiates an event photo detector from photo detectors contiguous to the event photo detector.

21. The method according to claim 20, wherein a permutation comprises a matrix photo detector and its horizontally and vertically adjacent photo detectors.

22. The method according to claim 20, wherein a permutation comprises a matrix photo detector and its horizontally, vertically, and diagonally adjacent photo detectors.

23. The method according to claim 21, wherein a permutation comprises a corner matrix photo detector and one horizontally and one vertically adjacent photo detector.

24. The method according to claim 21, wherein a permutation comprises a center matrix photo detector and two horizontally and two vertically adjacent photo detector.

25. The method according to claim 22, wherein a permutation comprises a corner matrix photo detector and one horizontally, one vertically, and one diagonally adjacent photo detector.

26. The method according to claim 22, wherein a permutation comprises a center matrix photo detector and two horizontally, two vertically, and four diagonally adjacent photo detector.

* * * * *